United States Patent
Fine et al.

(10) Patent No.: US 7,204,125 B2
(45) Date of Patent: Apr. 17, 2007

(54) PRESSURE ACTIVATED SAMPLING SYSTEM

(75) Inventors: David H. Fine, Lincoln, MA (US); Freeman W. Fraim, Lexington, MA (US)

(73) Assignee: L-3 Communications CyTerra Corporation, Orlando, FL (US)

( * ) Notice: Subject to any disclaimer, the term of this patent is extended or adjusted under 35 U.S.C. 154(b) by 0 days.

(21) Appl. No.: 11/087,818

(22) Filed: Mar. 24, 2005

(65) Prior Publication Data

US 2007/0062256 A1 Mar. 22, 2007

Related U.S. Application Data

(63) Continuation of application No. 10/316,746, filed on Dec. 11, 2002, now Pat. No. 6,895,801.

(60) Provisional application No. 60/338,705, filed on Dec. 11, 2001.

(51) Int. Cl.
  *G01N 30/72* (2006.01)
  *G01N 33/22* (2006.01)
  *G01N 35/10* (2006.01)
  *B01D 15/08* (2006.01)

(52) U.S. Cl. .......... 73/23.41; 73/23.2; 73/23.35; 73/31.01; 73/31.02; 73/31.03; 73/31.04; 73/863.22; 73/864.81; 73/23.4; 422/83; 422/89; 436/92; 436/104; 436/107; 436/111; 436/161; 436/901

(58) Field of Classification Search ........ 73/23.2, 73/23.22, 23.27, 23.35, 23.4, 23.41, 31.01–31.04, 73/863.22, 864.81, 864.91; 436/92, 104, 436/107, 111, 156, 901; 422/83, 89
See application file for complete search history.

(56) References Cited

U.S. PATENT DOCUMENTS

| 3,915,339 | A | 10/1975 | Matson |
| 4,580,440 | A | 4/1986 | Reid et al. ................ 73/31.07 |
| 5,585,575 | A | 12/1996 | Corrigan et al. |
| 5,795,544 | A | 8/1998 | Matz |
| 5,915,268 | A | 6/1999 | Linker et al. |
| 5,942,699 | A | 8/1999 | Ornath et al. ............ 73/863.21 |
| 6,295,860 | B1 | 10/2001 | Sakairi et al. |
| 6,324,927 | B1 | 12/2001 | Ornath et al. ............ 73/864.33 |
| 6,375,697 | B2 | 4/2002 | Davies |
| 6,610,977 | B2 | 8/2003 | Megerle |
| 2003/0033851 | A1 | 2/2003 | Gelfman et al. |
| 2003/0106362 | A1 | 6/2003 | Megerle et al. |

*Primary Examiner*—Daniel S. Larkin
(74) *Attorney, Agent, or Firm*—Fish & Richardson P.C.

(57) ABSTRACT

Screening of items for the presence of contaminants, such as explosives residue, is accomplished by subjecting an item loaded into a pressure chamber to a pressure substantially in excess of atmospheric pressure conditions and rapidly decompressing the item to the ambient atmospheric pressure. The rapid decompression serves to scavenge vapors and particles from the exterior and interior of the item and any objects it contains. A sample of the vapors and particles removed from the item by the rapid decompression is sampled and is tested to determine whether a predetermined contaminant is present in the sample. Depending on the types of contaminants for which the sample is tested, it is possible to detect whether explosives, biological or chemical agents, and/or narcotics residues are present on or in the item being screened.

9 Claims, 2 Drawing Sheets

PRESSURE ACTIVATED SAMPLING SYSTEM

CROSS-REFERENCE TO RELATED APPLICATIONS

This application is a continuation application of U.S. application Ser. No. 10/316,746, filed Dec. 11, 2002, now U.S. Pat. No. 6,895,801, which is a utility from U.S. provisional application Ser. No. 60/338,705, filed Dec. 11, 2001. This application claims priority to each of these prior applications, and the disclosures of the prior applications are considered part of (and are incorporated by reference in) the disclosure of this application.

TECHNICAL FIELD

This description relates to detection of dangerous or illegal materials, and more particularly to the automated detection of explosives and chemical and biological agents in luggage or other containers.

BACKGROUND

Airport security screening services protect travelers, air transportation personnel, facilities, and equipment against terrorist and other criminal acts. The heightened awareness of security in the aviation industry has resulted in added focus on the effectiveness of detecting explosives, chemical and biological agents, and other dangerous or illegal materials in luggage and other cargo. Explosives Detection Systems (EDS) have been deployed at airports across the U.S. for screening checked luggage. Most EDS screening uses Computer tomography (CTX) machines that rely upon imaging technology to detect explosives. In addition, Explosives Trace Detection (ETD) devices are currently being used to detect the presence of explosive materials in checked or carry-on bags. Prior to Sep. 11, 2001, EDS screening was primarily used for a relatively small number of checked bags belonging to passengers who were selected randomly or by a Computer Assisted Passenger Prescreening System (CAPPS). After September 11, a goal was set to achieve one hundred percent screening of all checked bags by Dec. 31, 2002.

For example, to facilitate comprehensive baggage screening in small airports or small screening stations at larger airports, the Transportation Security Administration (TSA) has developed the ARGUS EDS program, which is intended to be a low cost, low throughput bag inspection system. The program guidelines establish certain criteria for a new class of EDS. For example, the program requires a certain automated detection success rate, establishes a maximum false alarm rate, specifies a minimum throughput, and places restrictions on the size of the machine.

SUMMARY

Techniques are provided for screening items, such as luggage, mail, packages, or cargo containers, for contaminants, such as those that may evidence the presence of prohibited materials. An item to be screened is subjected to pressurization to a predetermined pressure level and then is subjected to rapid decompression to the ambient atmospheric pressure. The rapid decompression serves to strip particles and scavenge vapors from interior and exterior surfaces of the item and the contents of the item. These particles and vapors are sampled by a sample collection medium, which is then analyzed contaminants indicating the presence of explosives, biological agents, chemical agents, and/or narcotics.

In one general aspect, screening an item for the presence of contaminants can be accomplished by subjecting an item to a pressure substantially in excess of atmospheric pressure conditions and rapidly decompressing the item to the atmospheric pressure. A sample of a substance that includes either vapors or particles removed from the item by the rapid decompression is collected, and the sample is tested to determine whether a predetermined contaminant is present in the sample.

Implementations may include one or more of the following features. For example, subjecting the item to the pressure can include slowly increasing the pressure in a chamber from the atmospheric pressure to a selected pressure level. The rapid decompression of the item can include venting the chamber to the atmospheric pressure conditions. In different possible implementations, the selected pressure level can be at least about two atmospheres, at least about three atmospheres, or at least about five atmospheres. The chamber may be maintained at or near the selected pressure level until approximate pressure equilibrium is achieved. A series of pressure pulses can also be generated after approximate pressure equilibrium is achieved and before the rapid decompression occurs. Collecting a sample can include collecting samples of substances removed from the outside and the inside of the item by the rapid decompression. Collecting a sample can also include selectively collecting samples during a predetermined portion of a period in which the decompressing is performed.

In some implementations, a gas can be injected into the chamber subsequent to initiating the rapid decompression. During the injection of the gas, a sample of a substance removed from the item by the rapid decompression can be collected.

The testing of the sample can include performing ion mobility spectrometry and/or gas chromatography on the sample. The predetermined contaminant can be one of many predetermined contaminants. The testing can include testing the sample for an explosive, a chemical agent, a biological agent, and/or a narcotic.

The item can include an item of luggage, a cargo container, or another type of package or container, and the contaminants for which the screening is performed can represent prohibited materials. The pressure chamber can also be purged of substances removed from the luggage during the rapid decompression by releasing a gas into the pressure chamber while the pressure chamber is vented to the ambient atmosphere. Samples of substances can be collected at least in part during at least a portion of the purging the pressure chamber. Pressure pulses can be generated after the pressure chamber reaches the predetermined pressure level and before the rapid decompression. The collected samples can be tested for prohibited materials, such as explosives, chemical agents, biological agents, and narcotics.

In another general aspect, a system for screening items for contaminants includes a pressure chamber adapted to contain at least one item, a pressurized gas source, and a valve for venting the pressure chamber to an ambient atmosphere. In addition, a controller is operable to control a pressurization of the pressure chamber by the pressurized gas source and to control the valve to initiate a rapid decompression of the pressure chamber. A sample collector is positioned to collect samples of substances removed from the item by the rapid decompression, and a trace-level contaminant detector is operable to detect whether at least one contaminant is sampled by the sample collector.

Implementations may include one or more of the following features. For example, the pressurized gas source can include a compressor. The pressure chamber can include one or more doors for loading and unloading items into and out of the pressure chamber. The system can also include a conveyor for loading items into and unloading items from the pressure chamber through the one or more doors. The controller can be further operable to control the pressurization of the pressure chamber up to an approximate predetermined level and to maintain the approximate predetermined level until pressure equilibrium is achieved. The system can include a bladder or a piston operable to generate a series of pressure pulses after the pressure equilibrium is achieved and before the rapid decompression of the pressure chamber. The system can also include a pressure gauge, with the controller being operable to receive signals from the pressure gauge to determine when pressure equilibrium is achieved. A second gas source may be operable to inject gas into the pressure chamber to flush from the pressure chamber substances that are removed by the rapid decompression from the items in the pressure chamber. The trace-level contaminant detector can include an ion mobility spectrometry detector.

The details of a particular implementation is set forth in the accompanying drawings and the description below. Other features will be apparent from the description and drawings, and from the claims.

DESCRIPTION OF DRAWINGS

Like reference symbols in the various drawings indicate like elements.

DETAILED DESCRIPTION

A pressure activated sampling system (PASS) uses very fast decompression to scavenge and eject a trace-vapor sample from an explosive device in luggage or other containers onto a suitable collector. The collector is then analyzed using a TSA-approved trace detector to detect the presence of explosive material. The PASS; provides an automated sampling system that can be used for one hundred percent baggage screening and that provides significant advantages over current baggage screening systems. For example, the PASS can significantly increase throughput, require much less space, detect much smaller explosive devices, and be implemented at a much lower cost. The PASS does not require X-ray radiation and thus does not damage film. In addition, the PASS can identify the explosives detected and can be upgraded to simultaneously sample for both chemical and biological agents and other hazardous or illegal materials.

A PASS can also be used to screen other types of containers or packages and, in large-scale implementations, even large seagoing cargo containers. In general, the PASS includes a pressure chamber, a compressor, a sample collector, and a trace level detector. The object to be screened is placed in the pressure chamber, and the chamber is slowly pressurized (e.g., over about ten to twenty seconds) to at least about two atmospheres (or in other implementations to at least about three atmospheres, or to about five or six atmospheres). Pressure in excess of six atmospheres can be used, although it has not generally been found to improve the results. Once approximate pressure equilibrium is achieved, the pressure chamber is rapidly decompressed (e.g., at a rate that requires less than a second or even less than half a second to reach atmospheric pressure) by venting the chamber to the ambient atmosphere. The air rushing out of the chamber is sampled and presented to a trace detector for analysis.

Figure 1:
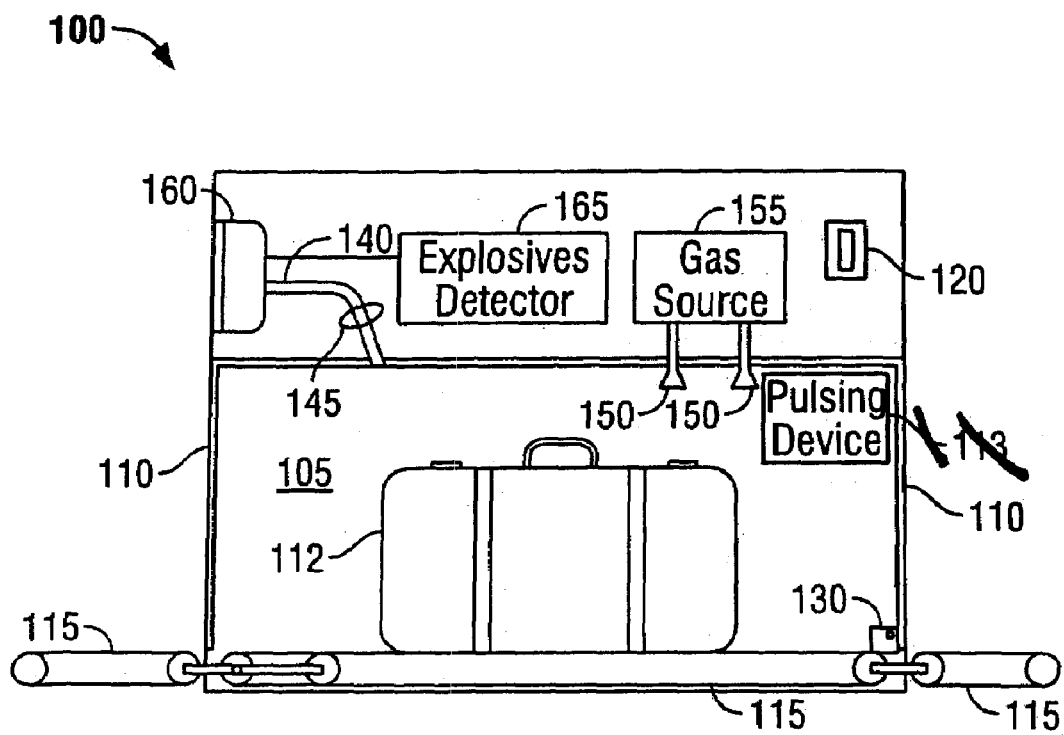
FIG. 1 is a schematic cross-sectional side view diagram of an automated pressure activated sampling system.
Figure 2:
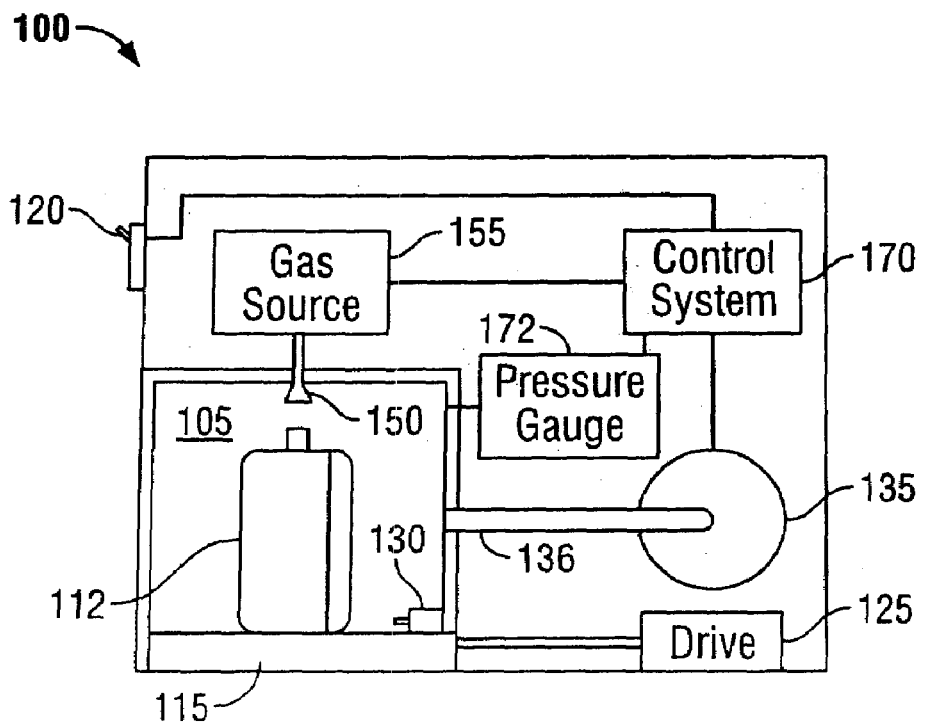
FIG. 2 is a schematic cross-sectional front view diagram of the automated pressure activated sampling system of FIG. 1.

FIG. 1 shows a schematic cross-sectional side view diagram of an automated PASS 100 and FIG. 2 shows a schematic cross-sectional front view diagram of the automated PASS 100. The PASS 100 includes a pressure chamber 105 that includes roll-up doors 110 that are fitted with pressure seals to prevent air from leaking out of the pressure chamber 105 around the edges of the doors 110. One implementation employs an off-the-shelf pressure vessel. For example, there are autoclave sterilization chambers with the proper dimensions and characteristics that are available virtually off-the-shelf. The pressure chamber 105 is sized to accommodate the largest possible bag. As a result, three to six conventionally sized bags can typically be loaded into the pressure chamber 105 simultaneously. This increases the throughput of the system and often allows all of an individual's or a family's luggage to be tested at the same time.

To perform screening, one or more pieces of luggage 112 are placed on a conveyor 115. An operator uses a switch 120 to activate a mechanical conveyor drive system 125 to load the luggage 112 into the pressure chamber 105. A light beam detector 130 or some other object detection mechanism automatically determines whether there are any straps or other objects that could interfere with the proper closing of the roll-up doors 110. The roll-up doors 110 close automatically, and safety interlocks are used to ensure that the pressure chamber 105 remains sealed during the pressurization process.

A compressor 135 slowly pressurizes the pressure chamber 105 through a pipe 136. The pressurization forces air into the interior of the luggage 112, including the interior of any improvised explosive device (IED) or electronic items inside the luggage 112. If a lower pressure is used, the length of time in which it takes to reach approximate pressure equilibrium may be longer relative to the length of time required with a higher pressure. For example, by pressurizing the pressure chamber 105 to about two to three atmospheres, pressure equilibrium may require about fifteen to twenty seconds. By slowly pressurizing the chamber to about five to six atmospheres over a period of about ten seconds, on the other hand, a pressure level can be quickly achieved inside the luggage 112 so that air stripping is more powerful. In addition, high-level pressurization provides more reliable penetration of tightly packed items that might otherwise form "seals" that prevent air from entering. The length of time required to reach pressure equilibrium may also depend on how tightly packed items are in the luggage 112. The pressure chamber 105 may be maintained at high pressure for as long as necessary to achieve pressure equilibrium. However, as discussed herein, pressure equilibrium does not require absolute equilibrium, but merely that the pressure in the pressure chamber reaches some degree of stability and is not changing significantly. Generally, this approximate pressure equilibrium can be achieved within about fifteen seconds at five to six atmospheres. In general, the pressurization is slow relative to the subsequent rapid decompression, with the rates of pressurization and decompression differing from one another by an order of magnitude or more.

In one implementation, pressure equilibrium is followed by a few seconds of pressure pulsing. Pressure pulsing generally involves varying the pressure by ten to twenty percent in either direction from the pressure equilibrium level. The pressure internal to the chamber can be pulsed using a piston or a bladder-type container inside the pressure chamber 105. Such pressure pulsing has the effect of pumping air into and out of the luggage 112, which enhances the collection of potential explosive particles.

Pressurization is followed by a rapid decompression, which is accomplished by venting the pressure chamber 105 to the ambient atmosphere. A vent 140 includes a valve 145 that is opened to allow the pressurized air within the pressure chamber 105 to escape at high velocity. The high air velocity and momentum changes associated with the rapid decompression effectively strip particles from surfaces both inside and outside of the luggage 112. In particular, the high velocity air overcomes particle adherence to surface and other boundary conditions that might otherwise prevent a particle from leaving the surface under low pressure vacuum or air sweeping. This disruption expels any traces of explosive residue from inside the luggage 112, including from the surface and surrounding air of any explosive charge itself, and creates an air mass that is enriched with vapors and particles.

Once the pressure chamber 105 reaches or is near the ambient air pressure, one or more gas nozzles 150 connected to a gas source 155 can be used to clear or purge the remaining particle-enriched and vapor-enriched air from the pressure chamber 105. Generally, the air that remains in the pressure chamber 105 after the decompression includes enhanced levels of vapors and particles scavenged from the luggage 112. During decompression, molecules are removed from surfaces through disruption of the air/surface boundary layer and end up being dispersed throughout the pressure chamber 105 after decompression. The purging process serves to effectively "sanitize" the pressure chamber 105 by expelling any residual particles and vapors from the pressure chamber 105. This helps prevent particles and vapors from contaminating the pressure chamber 105 during subsequent screening of other items of luggage. In addition, the residual particles and vapors that are expelled during this purging process can be sampled to test for explosive residue. In one implementation, the nozzles are oriented to direct the residual particles and vapors toward a sample collection medium. The gas used during the purging process can be either ambient or purified air or some type of inert gas, such as argon. In one implementation, a single compressor or gas source can be used in place of the gas source 155 and the compressor 135.

The vent 140 is fitted with one or more sample collection devices 160. During the initial stages of the decompression, when air velocity is very high, the sample flow is too high for use of an ordinary sample collection media. Accordingly, an impact-type collection system is used, in which particles are collected by impacting a plate, which, in different implementations, may be a metal plate or a soft and pliable surface. Two or more segments of the exit airflow can also be separately sampled. For example, during the later stages of the decompression and during the purging process, a filter, such as a high efficiency filter, may be used as the sample collection medium. Time selective sampling of the exit airflow may also be used to collect samples from the portion of the air that was in close contact with the contaminated surfaces. Generally, the air that escapes just as the pressure chamber 105 is vented does not have a significant amount of vaporous or molecular material from the luggage 112. Instead, the portion of the air stream that exits when the pressure in the pressure chamber 105 is near atmospheric pressure or during the gas purge is most heavily enriched with vapors and particles from the luggage 112 and its contents. Accordingly, samples may be collected only during these later stages of the overall process.

A trace-level explosives detector 165 next analyzes the collected sample or samples. In one implementation, the trace-level explosives detector 165 includes an ion mobility spectrometry (IMS) detector and performs a software-based analysis of the sample. Software algorithms that recognize explosives have already been developed for the FAA-approved trace-particle detectors. When ion mobility spectrometry is used, for example, the trace-level explosives detector 165 can analyze the output of the ion mobility spectrometry detector to determine whether any explosive material is present. When a filter is used to collect samples, the filter itself may be presented (either manually or automatically) for analysis by ion mobility spectrometry or gas chromatography in connection with chemiluminescence detection performed, for example, by the trace-level explosives detector 165. The output of the ion mobility spectrograph or the gas chromatograph then may be analyzed by software running on a microprocessor within the trace-level explosives detector 165.

Generally, the overall screening process can be performed by a control system 170 that is connected to and controls the conveyor drive system 125, the roll-up doors 110, the compressor 135, the valve 145, the gas source 155, and the trace-level explosives detector 165. In addition, the control system 170 is further connected to and activated by the switch 120. The control system 170 is generally implemented as a processor programmed to control the overall screening process.

In one implementation, the entire cycle of loading a bag into the system, pressurization, decompression, sample collection, analysis and ejection of the bag from the system takes about sixty seconds. At an average of at least three bags per cycle, one can expect a throughput of one hundred eighty bags per hour for a single pressure chamber 105. However, because the sampling and not the analysis is the rate determining step, at a small increase in cost, one analysis device can easily support two or more sampling front ends (i.e., pressure chambers 105) simultaneously, leading to an expected throughput of about three hundred sixty or more bags per hour.

The trace-level explosives detector 165 may include or be similar to existing trace-particle detectors that have been approved by the TSA for use with carry-on luggage. These detectors have been shown to be capable of reliably detecting and identifying trace residue that is presented to them. The interpretation of the output of these detectors is well developed and fully automated without human input. However, these detectors only work well if the outside of the luggage is contaminated with explosive residue and if the person that samples the object happens to scavenge the precise location of the residue. Thus, the effectiveness of these detectors is typically dependent upon the skill of the operator in obtaining a chance contamination on the outside of the luggage. A terrorist may have become aware of this limitation and taken precautions to ensure that there is little, if any, residue on the outside of the luggage. The described techniques, however, are independent of chance contamination on the outside or even on the inside of the suitcase, and instead rely on harvesting enough explosive residue from the main explosive charge of the IED itself.

Although generally described in connection with sampling for explosive residue, the techniques can also be used to sample other types of trace compounds from within a suitcase. By including other trace-level detectors, or by modifying the trace-level explosives detector 165 to recognize additional contaminants, the same equipment can be used to sample for other trace materials, such as chemical and biological agents and narcotics, although detection of biological agents may require other types of trace-level detectors, such as polymerase chain reaction or immunoassay detection systems.

Some prior approaches to sampling for contaminants have used both pressure and vacuum for sampling. The PASS uses pressure only, and achieves the same goal by decompressing to atmospheric pressure. The PASS has significant advantages over a dual pressure-vacuum system. For example, the PASS eliminates the need entirely for a very large vacuum pump. The rate of decompression can be significantly increased by using pressure alone, instead of relying upon the pumping capacity of the vacuum pump. In addition, there is no vacuum system to contaminate. The complexity and cost of the containment vessel and all the seals are greatly reduced because a pressure-only system does not have to handle both pressure and vacuum and does not require two-way valves. The use of a gas purge instead of a vacuum is also beneficial because the purging process displaces and concentrates the particle-enriched and vapor-enriched air.

Particularly in sampling large seagoing containers, ultrasonic vibration can also sometimes help loosen particles. Thus, some implementations may make use of ultrasonic vibration.

One implementation of the PASS sampling system is less than one quarter of the size of the TSA's EDS specifications and has seven times the throughput. Based on TSA data, the expected false alarm rate of approved trace detectors should be less than one percent. Operationally, low false alarms will translate into a significantly higher effective throughput, especially when compared to CTX's reported thirty percent rate of false alarms under typical usage conditions. Unlike systems that rely on density, which is a surrogate property, trace detectors rely for detection on the precise chemical structure of the explosive. This is the key reason why they have such a low false alarm rate.

Because of its effectiveness at scavenging explosive residue, the PASS is also capable of detecting IEDs containing one tenth to one hundredth of the amount of explosive that can be detected by current systems. There is also no radiation hazard presented by the PASS machinery. At the same time, the PASS is an inherently simple system, and should cost less than one third of current systems to produce in one hundred unit quantities. The basic components of PASS are industrial grade heavy equipment components, such as a compressor, simple pressure vessels, simple pressure seals, control valves, conventional gas plumbing fixtures and controls, conveyors, computers, and the like. These components are not only relative inexpensive, but they are also exceptionally reliable and readily available. The major components that need to be specially fabricated and tested are the pressure-vacuum chamber, the door mechanism, and the system operating software and controls. The mechanical simplicity translates into lower anticipated annual maintenance costs. Moreover, the PASS provides fully automatic data interpretation, which leads to shorter training and less room for human error.

The PASS can be deployed in different parts of the airport. It can be used as a stand-alone system or complementary to the CTX units currently used to make use of the strengths of both systems. Listed following are different possible deployment scenarios. The ideal scenario may be different for different airports, or even in different parts of the same airport.

The PASS may be deployed, for example, at a security check prior to baggage check-in. In this scenario, there is a large central security checkpoint, which may contain a multitude of stations, to check all carry on luggage. Passenger ID, and passenger profiling, if used, would occur at this stage. The use of the PASS could be integrated with a CTX device at the same location for improved security checks. After being cleared at the security checkpoints the passenger would then proceed to the baggage check-in counter. Since the average time for baggage check in is greater than the average time for the security check, fewer security check points may be required than the number of baggage check-in counters.

The PASS might alternatively be deployed at baggage check-in. In this scenario, the PASS would be integrated with the baggage check-in counter. If not fully automated, the baggage check in clerk would physically remove a small sample filter from the PASS and place it in the trace-level explosives detector 165.

The PASS could also be deployed at the carry-on security check. For additional security, a PASS device could be integrated along with the currently used X-ray equipment at the security check in gates of the airport, complementing the already installed equipment. It could be designed to make use of the currently existing trace explosives detection systems.

In another scenario, the PASS could be deployed at baggage handling and make up areas. One challenge at airports is the clearing of transfer luggage. The PASS would be ideal for this application, both as a stand alone, or complementary to the CTX units. It could be set up at any convenient area within the baggage make up area.

In one implementation, the PASS can be used in place of full-scale CTX systems. As an alternative, the PASS can also be designed to meet the target requirements of the TSA's ARGUS program. For example, the ARGUS specification lists both military and certain commercial explosives that are required to be detected. The three approved trace-level explosives detectors have all been shown to be capable of detecting plastic explosives, TNT, and NG. They have not been approved for detecting ammonium nitrate-based explosives and various black powders. Dynamite typically contains either NG and/or EGDN and is easily detected by the TSA-approved explosives detectors.

Additional windows need to be opened on the ion mobility detectors so that they can be tuned to detect certain constituents of ammonium nitrate, black powder, Pyrodex, single-based propellants, double-based propellants, and triple-based propellants. In addition, various stabilizers are added to ammonium nitrate-based explosives that can also be detected by ion mobility detectors.

Black powder always contains sulfur, which can be detected by means of its oxidation products, $SO_2$ or $SO_3$. In addition, these formulations generally contain trace residues of DNT and/or NG, which can be detected using standard ion mobility. A less flammable black powder substitute is Pyrodex. It is shipped as a flammable solid, instead of as a Class A explosive. In addition to sulfur, Pyrodex also contains sodium benzoate and sodium dicyanamide, which are amenable to detection by ion mobility.

Single-based propellants are typically made from nitrocellulose, with traces of 2,4,DNT. Common impurities include diphenylamine and ethylcentralite, both of which can be detected by ion mobility. Double-based propellants, by definition, contain either NG or EGDN, both of which are detected by standard ion mobility. Triple-based propellants typically contain nitroguanadine as well as NG.

The ARGUS specification also requires that the explosives detection system accept bag sizes up to 92 cm×75 cm×51 cm. In general, the system is designed to accept the largest possible bag. This target-sized bag is significantly larger than the typical bag. The target size would result in a volume that would accommodate three to six bags of a more conventional size, which would allow for the screening of a typical family unit's checked luggage in one large sample at the time of check in.

The ARGUS specification requires throughput of at least fifty bags per hour. As discussed above, the PASS should be able to accommodate a throughput of at least one hundred eighty bags per hour per chamber. Thus, a dual pressure chamber PASS would provide an expected throughput of about three hundred sixty bags per hour.

The ARGUS specification, because of its focus on smaller airports and small screening stations, requires the ability to provide single-sided access to the screening apparatus. The nature of the design of the PASS is such that it can be configured for single-sided or flow-through (i.e., two-sided) access, depending upon the desired configuration for a given installation. In a single-sided implementation, the luggage 112 could be ejected from the same side and through the same door 110 as used for loading the luggage 112 into the pressure chamber 105. A PASS that provides flow-through access, on the other hand, could include a conveyor system that loads the luggage 112 into the apparatus through a first door 110 on one side and ejects the luggage 112 through a second door 110 on another side (as depicted in FIG. 1). Unlike a CTX system, the PASS conveyor should be only a few inches off the floor. The only item that resides under the conveyor 115 will be the mechanical drives for the conveyor 115, and possibly the vibration machinery, if it is included. This low conveyor height will make it easier for passengers to load their own bags on the feed conveyor 115, which should be at floor level.

Another requirement of the ARGUS specification is that the system's footprint is not to exceed 210 cm×335 cm. The needed footprint for a CTX system is seven square meters. By comparison, the PASS can be implemented in an apparatus that has a footprint of about 128 by 162 cm, or two square meters, which is roughly 30% of the space required for a CTX system. In addition, the PASS can be implemented with a height that is approximately half that needed for a CTX system. In one implementation, it is possible to take advantage of the allowable height to have the doors 110 of the pressure chamber 105 either move vertically up and down, or even possibly be inside the pressure chamber 105 and open in a similar manner to a garage door. In addition, much of the system utilities and pressure pumps can be located above the pressure chamber(s) 105.

Figure 3:
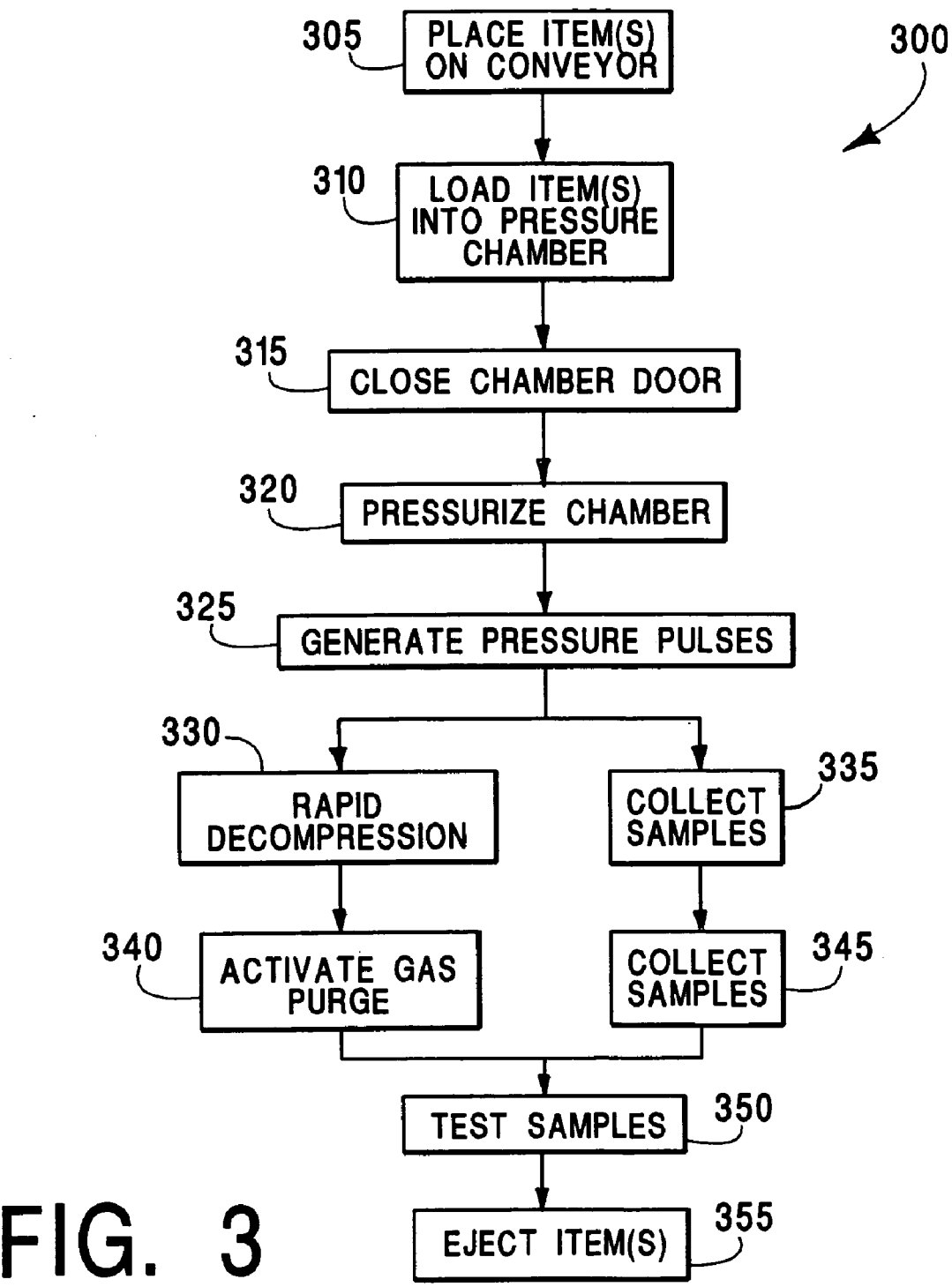
FIG. 3 is a flow diagram of a process for screening a container for contaminants.

FIG. 3 illustrates a process 300 for screening a container, such as an item of luggage 112, for contaminants. First, a passenger or an operator of the screening apparatus places one or more items on a conveyor 115 (step 305). The operator presses a button that causes the conveyor to propel the items into a pressure chamber 105 (step 310). Automatic light beams determine whether there are any trailing straps that could interfere with the proper closing of the pressure chamber door 110, and the pressure chamber door 110 closes automatically (step 315).

Once the door 110 is closed and any integrated safety locks are engaged, the automated sampling process is initiated with a slow pressurization of the pressure chamber 105 (step 320). Once the pressure chamber 105 reaches a predetermined pressure level, the pressurization is maintained for a period of time sufficient to allow the pressure chamber to reach approximate pressure equilibrium. This period of time can be predetermined based, for example, on empirical data from experimental tests or simulations. Alternatively, a pressure gauge 172 can provide, to a control system for the apparatus, control signals indicating the pressure level. By waiting for the control signals to indicate that the pressure level inside the pressure chamber 105 has somewhat stabilized (i.e., that the pressure has stopped dropping), it can be determined when the approximate pressure equilibrium is reached. In some implementations, after the pressure equilibrium is achieved, a series of pressure pulses are generated (step 325).

Next, rapid decompression is initiated by venting the pressure chamber 105 to the ambient atmosphere (step 330). Simultaneously with the decompression or a portion thereof, particle and/or vapor samples are collected (step 335). The samples may be collected by one or more different collection media (e.g., an impactor-style collector and/or a filter-type collector). In addition, the samples may be collected only during a stage or stages of the decompression in which vapors and particles from the exterior or interior of the items being tested are expected to be present. Once the pressure chamber 105 is at or near atmospheric pressure, a gas purge is initiated by rapidly opening a valve through which pressurized air or other gas is released into the pressure chamber 105, thereby clearing any remaining particle-enriched or vapor-enriched air from the pressure chamber (step 340). Samples are again collected simultaneously with the gas purge (step 345) using either the same collection medium or media used in step 335 or a different collection medium or media.

Once the pressure chamber 105 is fully decompressed and the gas purge is complete, the samples are then tested for contaminants that might evidence the presence of explosives, biological or chemical agents, and/or narcotics (step 350). In one implementation, the operator removes a small material sample filter from a sample holder and places the filter in an ion mobility detector or a gas chromatograph coupled with a chemiluminescence detector. The analyzer automatically carries out its analysis and displays the result as PASS or FAIL. A FAIL could also be accompanied by a description of the type of explosive or other contaminant that had been found. In an alternative implementation, the testing of the sample can be performed by automatically transferring the sample to the analysis device without human intervention. At the end of the sampling cycle, the pressure chamber door 110 opens, and the item or items are automatically ejected or the operator ejects the item or items by pressing a button (step 355). The system would then be ready for the next passenger.

Although illustrated and described in a particular order, the process steps need not be performed in the order specified. For example, testing of one or more samples may begin before the gas purge of step 340 is complete. Alternatively, sample testing might not occur until after the item is ejected at step 355.

A number of implementations have been described. Nevertheless, it will be understood that various modifications may be made. For example, the techniques may be applied in the context of testing large cargo containers or other items for contaminants of any kind. In addition, the techniques may be used in connection with heat, vibration, CAT scans, or X-rays, which may, in some implementations, provide some assistance in detecting contaminants. Furthermore, instead of using atmospheric air to pressurize the pressure chamber, some other type of gas, such as an inert gas or purified air, can be used. Accordingly, other implementations are within the scope of the following claims.

What is claimed is:

1. A system for screening items for contaminants, the system comprising:
    first and second pressure chambers, the first pressure chamber being adapted to contain at least a first item and the second pressure chamber being adapted to contain at least a second item;
    at least one pressurized gas source connected to provide pressurized gas to the pressure chambers;
    valves connected to vent the pressure chambers to an ambient atmosphere;
    a controller operable to control pressurization of the pressure chambers by the at least one pressurized gas source and to control the valves to initiate rapid decompression of the pressure chambers;
    at least one sample collector positioned to collect samples of substances removed from the first and second items by the rapid decompression; and
    a trace-level contaminant detector operable to detect whether at least one contaminant is sampled by the at least one sample collector.

2. The system of claim 1 wherein the at least one pressurized gas source comprises a compressor.

3. The system of claim 1 wherein the first pressure chamber includes at least one door for loading and unloading the first item into and out of the pressure chamber.

4. The system of claim 3 further comprising a conveyor for loading items into and unloading items from the first pressure chamber through the at least one door.

5. The system of claim 1 wherein the controller is further operable to control the pressurization of the first pressure chamber up to an approximate predetermined level and to maintain the approximate predetermined level until an approximate pressure equilibrium is achieved.

6. The system of claim 5 further comprising at least one of a bladder or a piston operable to generate a series of pressure pulses after the approximate pressure equilibrium is achieved and before the rapid decompression of the first pressure chamber.

7. The system of claim 5 further comprising a pressure gauge, wherein the controller is further operable to receive signals from the pressure gauge to determine when the approximate pressure equilibrium is achieved.

8. The system of claim 1 further comprising a second gas source operable to inject gas into the first pressure chamber to flush from the first pressure chamber substances that are removed from the at least one item by the rapid decompression.

9. The system of claim 1 wherein the trace-level contaminant detector comprises an ion mobility spectrometry detector.

* * * * *